*(12)* United States Patent
Park et al.

(10) Patent No.: US 10,836,795 B2
(45) Date of Patent: Nov. 17, 2020

(54) DUAL FUNCTIONAL NOVEL PEPTIDE HAVING CELL PERMEABILITY AND BONE TISSUE REGENERATION ABILITY, AND USE THEREOF

(71) Applicants: SEOUL NATIONAL UNIVERSITY R&DB FOUNDATION, Seoul (KR); NANO INTELLIGENT BIOMEDICAL ENGINEERING CORPORATION. CO. LTD, Chungcheongbuk-do (KR)

(72) Inventors: Yoon Jeong Park, Seoul (KR); Chong-Pyoung Chung, Seoul (KR); Jue-Yeon Lee, Gyeonggi-do (KR); Joocheol Park, Seoul (KR)

(73) Assignees: SEOUL NATIONAL UNIVERSITY R&DB FOUNDATION, Seoul (KR); NANO INTELLIGENT BIOMEDICAL ENGINEERING CORPORATION CO. LTD., Chungcheongbuk-Do (KR)

( * ) Notice: Subject to any disclaimer, the term of this patent is extended or adjusted under 35 U.S.C. 154(b) by 0 days.

(21) Appl. No.: 16/464,099

(22) PCT Filed: Dec. 27, 2017

(86) PCT No.: PCT/KR2017/015588
§ 371 (c)(1),
(2) Date: May 24, 2019

(87) PCT Pub. No.: WO2018/124749
PCT Pub. Date: Jul. 5, 2018

(65) Prior Publication Data
US 2019/0382446 A1  Dec. 19, 2019

(30) Foreign Application Priority Data
Dec. 27, 2016  (KR) ................. 10-2016-0180121

(51) Int. Cl.
*A61K 38/08*  (2019.01)
*A61K 38/00*  (2006.01)
*A61K 9/06*  (2006.01)
*A61K 9/00*  (2006.01)
*C07K 7/06*  (2006.01)
*A61P 19/00*  (2006.01)
*A61P 19/08*  (2006.01)
*A61L 27/22*  (2006.01)

(52) U.S. Cl.
CPC ............. *C07K 7/06* (2013.01); *A61K 9/0014* (2013.01); *A61K 9/06* (2013.01); *A61L 27/22* (2013.01); *A61P 19/08* (2018.01); *A61K 38/00* (2013.01); *A61L 2430/02* (2013.01); *C07K 2319/00* (2013.01)

(58) Field of Classification Search
CPC ...... A61K 38/00; A61K 38/08; A61K 9/0014; A61K 9/00; A61K 9/06; A61P 19/08; C07K 7/06; C07K 2319/00
USPC ................. 514/1.1, 16.7, 21.6; 530/300, 328
See application file for complete search history.

(56) References Cited

U.S. PATENT DOCUMENTS 7,745,391 B2 * 6/2010 Mintz ..................... A61P 31/00
514/19.3
2016/0060319 A1   3/2016 Jo et al.

FOREIGN PATENT DOCUMENTS

| KR | 1020120026408 A | 3/2012 |
| KR | 1020130049793 B1 | 7/2013 |
| KR | 1020130031870 B1 | 6/2014 |
| KR | 1020140115121 A | 9/2014 |
| KR | 1020150145470 A | 12/2015 |

OTHER PUBLICATIONS

Lee et al., "Identification of cell-penetrating osteogenic peptide from copine-7 protein and its delivery system for enhanced bond formation," J. Biomed Mater Res., 2019, 107(11): 2392-2402. (Year: 2019).*
Q9UBL6 from UniProtKB, pp. 1-12. Integrated into UniProtKB/Swiss-Prot on Dec. 1, 2000. (Year: 2000).*
McIntosh J., "Collagen—What is it and what are its uses," from https://www.medicalnewstoday.com/articles/26881, pp. 1-10. Accessed Feb. 16, 2020. (Year: 2020).*
Varshosaz et al., "Development of bioadhesive chitosan gels for topical delivery of lidocaine," Sci. Pharm., 2006, 74: 209-223 (Year: 2006).*
Lee, Ji-Hyun, et al., "Odontogenic differentiation of human dental pulp stem cells induced by preameloblast-derived factors", "Biomaterials", 2011, pp. 9696-9706, vol. 32, Publisher: Elsevier.

(Continued)

*Primary Examiner* — Julie Ha
(74) *Attorney, Agent, or Firm* — Hultquist, PLLC; Steven J. Hultquist

(57) ABSTRACT

A peptide derived from the copine 7 protein and having both cell permeability and bone tissue regeneration ability, and a use of the peptide, are described. The peptide has excellent bone tissue regeneration ability and is therefore useful for treating a disease requiring bone regeneration, such as osteoporosis. Particularly, by also having cell permeability, the peptide does not require the attachment of a separate peptide or addition of another preparation for the cell permeation thereof and thus can be conveniently applied in orthopedics and the like requiring various surgical regeneration treatments.

9 Claims, 10 Drawing Sheets
Specification includes a Sequence Listing.

(56) References Cited

OTHER PUBLICATIONS

Nalefski, E., et al., "The C2 domain calcium-binding motif: Structural and functional diversity", "Protein Science", 1996, pp. 2375-2390, vol. 5, Publisher: Cambridge University Press.

"GenBank Accession No. XP_011751707.1", "NCBI Gen Bank", Mar. 30, 2015.

Oh, Hyun-Jung, et al., "CPNE7, a preameloblast-derived factor, regulates odontobastic differentiation of mesenchymal stem cells", "Biomaterials", 2015, pp. 208-217, vol. 37, Publisher: Elsevier.

Perestenko, P., et al., "The second C2-domain of copine-2, copine-6 and copine-7 is responsible for their calcium-dependent membrane association", "The FEBS Journal", 2015, vol. 282, No. 3722-3736, Publisher: Medical Research Council Brain Network Dynamics Unit at the University of Oxford, UK.

Springer, T., "Complement and the Multifaceted Functions of VWA and Integrin I Domains", "Structure", 2006, pp. 1611-1616, vol. 14, Publisher: Elsevier.

\* cited by examiner

SEQ ID NO: 4 Peptide 20mg 12.5X　　　　　　　　　　　　20X

SEQ ID NO: 4 Peptide 40mg 12.5X　　　　　　　　　　　　20X

Coprine 7 Protein 100ug 12.5X    20X

Coprine 7 Protein 200ug 12.5X    20X

```
                        SEQUENCE LISTING

<160> NUMBER OF SEQ ID NOS: 6

<210> SEQ ID NO 1
<211> LENGTH: 10
<212> TYPE: PRT
<213> ORGANISM: Artificial Sequence
<220> FEATURE:
<223> OTHER INFORMATION: Dual functional candidate peptide for cell
      penetration and bone tissue regeneration

<400> SEQUENCE: 1

Ser Thr Thr Phe Glu Glu Met Gln Lys Ala
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Dual functional candidate peptide for cell
      penetration and bone tissue regeneration

<400> SEQUENCE: 2

Phe Glu Glu Gly Gln Ala Gln Trp Asp Cys
1               5                   10

<210> SEQ ID NO 3
<211> LENGTH: 20
<212> TYPE: PRT
<213> ORGANISM: Artificial Sequence
<220> FEATURE:
<223> OTHER INFORMATION: Dual functional candidate peptide for cell
      penetration and bone tissue regeneration

<400> SEQUENCE: 3

Phe Glu Glu Gly Gln Ala Gln Trp Asp Cys Val Asn Pro Lys Tyr Lys
1               5                   10                  15

Gln Lys Arg Arg
            20

<210> SEQ ID NO 4
<211> LENGTH: 10
<212> TYPE: PRT
<213> ORGANISM: Artificial Sequence
<220> FEATURE:
<223> OTHER INFORMATION: Dual functional peptide for cell penetration
      and bone tissue regeneration

<400> SEQUENCE: 4

Val Asn Pro Lys Tyr Lys Gln Lys Arg Arg
```

```
<210> SEQ ID NO 5
<211> LENGTH: 10
<212> TYPE: PRT
<213> ORGANISM: Artificial Sequence
<220> FEATURE:
<223> OTHER INFORMATION: Dual functional candidate peptide for cell
      penetration and bone tissue regeneration

<400> SEQUENCE: 5

Ser Tyr Lys Asn Ser Gly Val Val Val Leu
1               5                   10

<210> SEQ ID NO 6
<211> LENGTH: 20
<212> TYPE: PRT
<213> ORGANISM: Artificial Sequence
<220> FEATURE:
<223> OTHER INFORMATION: Dual functional candidate peptide for cell
      penetration and bone tissue regeneration

<400> SEQUENCE: 6

Val Asn Pro Lys Tyr Lys Gln Lys Arg Arg Ser Tyr Lys Asn Ser Gly
1               5                   10                  15

Val Val Val Leu
            20
```

DUAL FUNCTIONAL NOVEL PEPTIDE HAVING CELL PERMEABILITY AND BONE TISSUE REGENERATION ABILITY, AND USE THEREOF

CROSS-REFERENCE TO RELATED APPLICATIONS

This is a U.S. national phase under the provisions of 35 U.S.C. § 371 of International Patent Application No. PCT/KR17/15588 filed Dec. 27, 2017, which in turn claims priority of Korean Patent Application No. 10-2016-0180121 filed Dec. 27, 2016. The disclosures of such international patent application and Korean priority patent application are hereby incorporated herein by reference in their respective entireties, for all purposes.

TECHNICAL FIELD

The present invention relates to a novel dual functional peptide having both cell permeability and bone tissue regeneration ability and the use thereof, and more particularly, to a novel peptide derived from copine 7 protein having both cell permeability and bone tissue regeneration ability and the use thereof as a bone implant material or the like.

BACKGROUND ART

Human tissues are classified into hard tissues such as bones and soft tissues such as skin, mucous membranes and dental pulp. Collagenous fibrils (type I collagen fibrils) are known to play a major role in determining the structure of hard tissues. A representative disorder associated with bone loss is osteoporosis, and tumors or the like can lead to damage to hard tissues.

In the fields of orthopedic and plastic surgery, guided bone regeneration, autograft, allograft, and the like, using various types of bone graft materials and barrier membranes, have been performed in order to restore lost bone tissues and fix bone defects after tumor treatment. However, these treatments are incapable of inducing sufficient regeneration effects. Recently, bone regeneration methods using various kinds of growth factors and proteins have been studied. However, bone morphogenetic protein-2, which is a protein typically used for bone regeneration in orthopedic surgery, has excellent bone regeneration capability, but has been reported to have a side effect of causing bone formation in tissues other than bone tissues and ultimately lead to death of patients, and to have another side effect of causing cancer. In addition, most drugs used for bone regeneration are based on the mechanism of bone absorption inhibition. Parathyroid hormone (PTH), which is the only drug used as a bone regeneration mechanism-based drug, is inconvenient in that it requires daily injection when used as a drug, since it is a protein having a very short half-life of a few minutes or shorter.

Meanwhile, recently, it has been demonstrated that copine 7 protein plays a role in differentiating dental pulp stem cells (DPSCs) into odontoblasts (Oh, Hyun-jung, et al. Biomaterials 37 (2015) 217, Lee, Ji-Hyun, et al., Biomaterials 32.36 (2011): 9696-9706). However, since the protein has a very short half-life in vivo, like other proteins, and is composed of a total of 633 amino acids, a complicated process of gene recombination is required in order to produce the protein. This acts as an obstacle to mass synthesis for use of the protein as a drug.

Accordingly, as a result of intensive efforts to solve the problems of the prior art as described above, the present inventors have identified that the sequence of a specific peptide of copine 7 protein has cell permeability and functions to improve bone regeneration. Based on this finding, the present invention has been completed.

DISCLOSURE

Technical Problem

Therefore, the present invention has been made in view of the above problems, and it is one object of the present invention to provide a novel peptide having dual functions of cell permeability and bone tissue regeneration ability.

It is another object of the present invention to provide a novel pharmaceutical composition for bone tissue regeneration treatment.

It is another object of the present invention to provide a novel biomaterial.

Technical Solution

In accordance with the present invention, the above and other objects can be accomplished by the provision of a peptide represented by an amino acid sequence of SEQ ID NO: 4.

In accordance with another aspect of the present invention, provided is a novel pharmaceutical composition for bone tissue regeneration treatment comprising the peptide as an active ingredient.

In accordance with another aspect of the present invention, provided is a bio-material comprising the peptide.

In accordance with another aspect of the present invention, provided is the use of the peptide, the pharmaceutical composition or the bio-material for bone tissue regeneration treatment.

In accordance with another aspect of the present invention, provided is a bone tissue regeneration treatment method including administering or grafting the peptide, the pharmaceutical composition or the bio-material to a patient in need of treatment of bone tissue regeneration.

BRIEF DESCRIPTION OF THE DRAWINGS

The above and other objects, features and other advantages of the present invention will be more clearly understood from the following detailed description taken in conjunction with the accompanying drawings, in which.

BEST MODE

Figure 1:
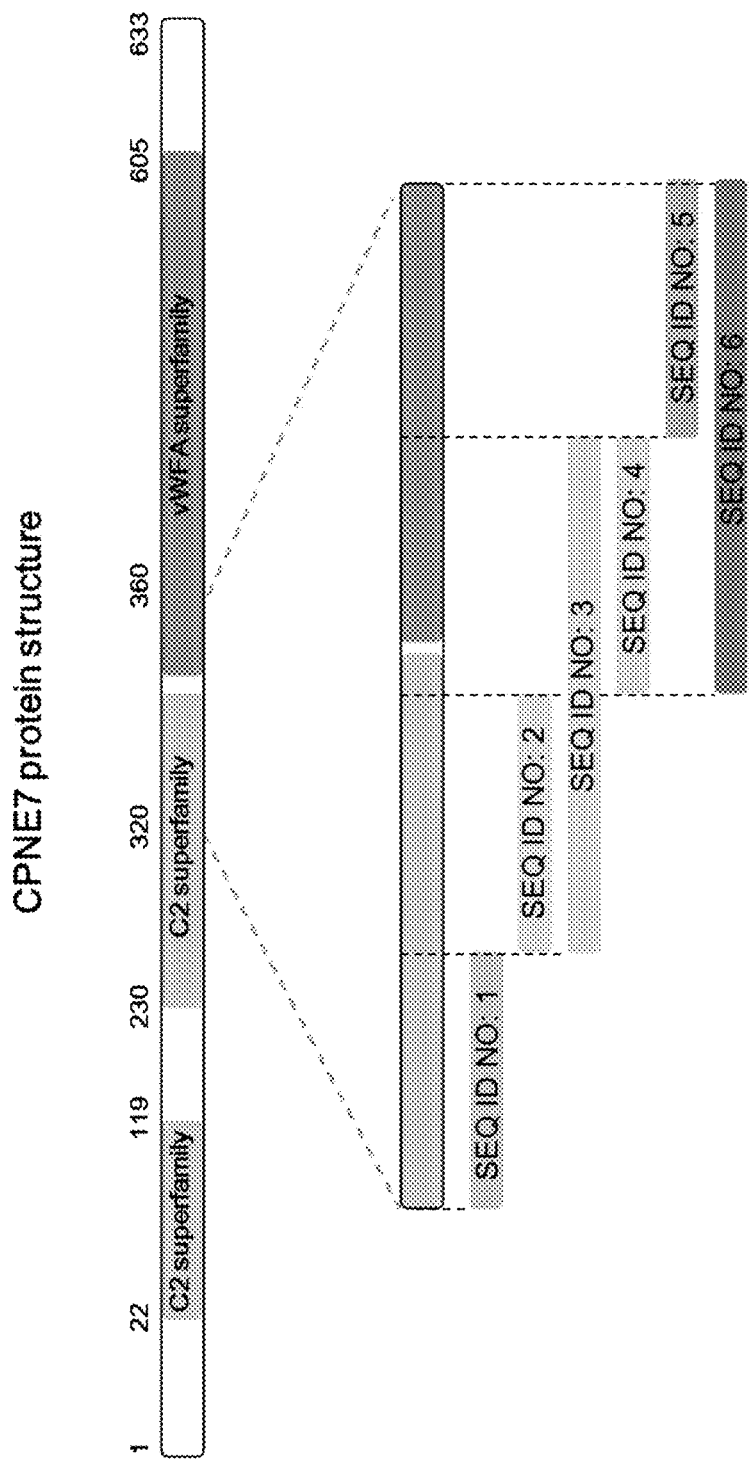
FIG. 1 shows the positions of peptides represented by amino acid sequences set forth in SEQ ID NOS: 1 to 6 on copine 7 protein.

Unless defined otherwise, all technical and scientific terms used herein have the same meanings as appreciated by those skilled in the field to which the present invention pertains. In general, the nomenclature used herein is well-known in the art and is ordinarily used.

The copine 7 protein is known to consist of two C2 domains and one vWMA domain, wherein the C2 domains are involved in intracellular entry by endocytosis using an extracellular matrix membrane, and contribute to both phosphorylation of the protein and structural stability of the protein by bonding to two or three calcium ions ($Ca^{2+}$) (Nalefski, Eric A., and Joseph J. Falke. Protein Science 5.12 (1996): 2375-239; Perestenko, Pavel, et al., FEBS journal 282.19 2015): 3722-3736). Meanwhile, the vWMA domain is known to be involved in cell adhesion in extracellular matrix proteins and integrin receptors and to regulate signal transduction and interactions between intracellular proteins (Springer, Timothy A. Structure 14.11 (2006): 1611-1616). Recently, it has been reported that copine 7 protein promotes the expression of the intracellular marker, dentin sialophosphoprotein (DSP) [Oh, Hyun-Jung, et al. Biomaterials (2015): 208-217; Lee, Ji-Hyun, et al. Biomaterials 32.36 (2011): 9696-9706)]. In addition, the present inventors previously identified that the expression of TAZ and Smad, which are intracellular bone differentiation markers, is increased by the copine 7 protein.

In conclusion of the study results, the present inventors have hypothesized that the copine 7 protein can induce bone differentiation through interaction between intracellular proteins, found a domain having intracellular permeation ability in the copine 7 protein, designed six peptides represented by the amino acid sequences of SEQ ID NOS: 1 to 6, and obtained peptides having the best effect by comparing the toxicity, cell permeability and bone regeneration ability of the peptides.

Accordingly, in one aspect, the present invention is directed to a peptide represented by an amino acid sequence set forth in SEQ ID NO: 4.

The peptide may have dual functions of cell permeability and bone tissue regeneration ability.

In the present invention, the peptide is preferably produced through chemical synthesis using a peptide synthesizer since the peptide can be produced in larger quantities compared to production of the copine 7 protein through a gene recombination technique, but the present invention is not limited thereto. Meanwhile, the peptide can be modified with D-type amino acids and other chemical substances in order to increase the stability in the human body or to maintain an active structure.

Meanwhile, the present inventors have identified through in-vitro experiments that the peptide promotes differentiation into bone tissues from stem cells present in bone defect parts and maximizes tissue regeneration ability without cytotoxicity.

Accordingly, in one aspect, the present invention is directed to a novel pharmaceutical composition for bone tissue regeneration treatment containing the peptide as an active ingredient.

As used herein, the term "treatment" refers to any action for treating a bone disease by administering a pharmaceutical composition containing the peptide as an active ingredient to a subject in need of bone regeneration (for example, an osteoporosis patient) in order to promote bone regeneration.

In the present invention, the composition may be formulated as the one selected from the group consisting of a formulation for oral administration, a formulation for injection or a gel formulation for topical implantation, but the present invention is not limited thereto, and can be prepared into a suitable formulation using any method well-known in the art (Joseph Price Remington, Remington's Pharmaceutical Science; 17th edition, MackPublishing Company, Easton Pa.).

In the present invention, the gel formulation for topical implantation may include: i) a synthetic polymer selected from the group consisting of polylactic glycolic acid, a poloxamer and propylene glycol; or ii) a natural polymer selected from the group consisting of collagen, alginic acid, propylene glycol alginate, chondroitin sulfate and chitosan, but is not limited thereto. Among them, alginic acid is a biocompatible and nontoxic natural polysaccharide which is a known biocompatible material that has been proven to be safe for various applications such as drug delivery systems, cell implantation carriers and wound therapeutics.

In an embodiment of the present invention to incorporate the peptide into a gel base, the peptide may be prepared by mixing a peptide with an alginic acid solution. Peptide may be further added to a peptide-alginic acid conjugate solution prepared by forming an ester bond between a peptide and alginic acid using a cross linker.

In one embodiment of the present invention, the concentration of alginic acid for preparing the gel formulation for topical implantation is preferably 5 to 10% (w/v), and more preferably 6 to 8%. Alginic acid may be dissolved in a tripolyphosphate solution and then calcium sulfate may be added thereto in order to provide calcium and phosphate ions, which are inorganic ions necessary for bone regeneration. The concentration of tripolyphosphate is preferably 1 to 10% (w/v), more preferably 4 to 6%. The calcium sulfate is preferably added at a concentration of 1 to 20 mg/mL, and more preferably at a concentration of 2 to 10 mg/mL.

The composition is preferably administered at a dose of 1 to 60 mg per 1 kg of a body weight of a subject in need of treatment, but the present invention is not limited thereto. The dose may vary depending on a variety of factors including the body weight, age, gender, health conditions and diet of the patient, administration time, administration method, excretion rate, and the severity of the disease. The dose can be determined in consideration of these factors by an ordinary expert in the art.

In the present invention, preferably, the peptide is used in units of mg for the composition. Copine 7 protein, from which the present peptide is derived, is readily degraded by intracellular enzymes and thus is not stable in the human body since it has a size of several tens of kDa, is impossible to mass-produce through synthesis since it is generally synthesized as a recombinant protein, and is used in units of ug, since it has a side effect of causing immune reactions in the body. However, in the present invention, it is found that the peptide has no cytotoxicity even when it is used in units of mg, mass production is possible and there is no difficulty in supplying the peptide, since it can be obtained through extracellular synthesis such as chemical synthesis. In particular, in the case of the peptide described above, when comparing doses of 20 mg and 40 mg, it was found that bone regeneration ability was maximized at a dose of 20 mg.

In the present invention, the composition may further contain at least one adjuvant selected from the group consisting of an excipient, a buffer, an antimicrobial antiseptic, a surfactant, an antioxidant, a tonicity adjuster, a preservative, a thickener and a viscosity modifier, but the present invention is not limited thereto. Each ingredient can be selected from a raw material commonly used in the art and suitably modified and used within the range acceptable for the art.

In the present invention, the composition may be administered as an individual therapeutic agent or in combination with another therapeutic agent, and may be administered sequentially or simultaneously with a conventional therapeutic agent. In addition, the composition may be used alone or in combination with another bone graft (implant) material. The bone graft material may include a bone mineral powder and a porous block thereof, a synthetic hydroxyapatite powder and a porous block thereof, a tricalcium phosphate powder and a porous block thereof, a monocalcium phosphate powder and a porous block thereof, and the like.

Finally, the present inventors identified that grafting of the bone graft material containing the peptide into a skull defect part of a rabbit resulted in a remarkable effect of regenerating new bones around the skull defect part of the rabbit.

Accordingly, in another aspect, the present invention is directed to a bio-material containing the peptide.

In the present invention, the biomaterial can be used as any kind and form of bone graft material and polymer scaffold used in the art. Preferably, the biomaterial is a biomaterial for bone graft containing a bone mineral powder derived from an autogenous bone, a cow bone or a pig bone and a porous block thereof, a synthetic hydroxyapatite powder and a porous block thereof, a tricalcium phosphate powder and a porous block thereof, a monocalcium phosphate powder and a porous block thereof, or silicon dioxide (silica) as a main ingredient, a bone-filling graft material containing a mixture of silica and a polymer as a main ingredient, a biocompatible polymer containing chitosan, a fine particle as a main ingredient, titanium or the like. In addition, the polymer scaffold is preferably a porous scaffold containing chitosan, a biocompatible polymer as a main ingredient, a three-dimensional porous scaffold of titanium, or the like. At this time, it is preferable that the surface of the bio-material and the scaffold for bone graft be modified so that the active peptide can be easily adhered thereto.

In the present invention, the biomaterial is preferably selected from the group consisting of natural polymers, bone minerals and synthetic polymers, but is not limited thereto.

In the present invention, the natural polymer is preferably selected from the group consisting of collagen, alginic acid, propylene glycol, chondroitin sulfate and chitosan, but is not limited thereto.

In the present invention, the bone mineral may preferably be i) derived from an animal or ii) chemically synthesized, but is not limited thereto.

In the present invention, the chemically synthesized bone mineral is preferably hydroxyapatite, but is not limited thereto.

In the present invention, the synthetic polymer is preferably selected from the group consisting of polylactic glycolic acid, a poloxamer and propylene glycol, but is not limited thereto.

In the present invention, the biomaterial is preferably used for bone graft, but is not limited thereto. In another aspect, the present invention is directed to the use of the peptide, pharmaceutical composition or the biomaterial for bone tissue regeneration treatment.

In another aspect, the present invention is directed to a method for bone tissue regeneration treatment including administering or grafting the peptide, the pharmaceutical composition or the biomaterial to a patient in need of treatment of bone tissue regeneration.

Since the pharmaceutical composition and administration method used in the method for bone regeneration treatment have been described above, repeated description thereof will be omitted in order to avoid excessive complexity and a general method used for bone regeneration treatment can be used through appropriate implementation or modification by those skilled in the art.

Meanwhile, the subject to which the pharmaceutical composition is administered or to which the biomaterial can be grafted may be any animal including human, and may be, for example, an animal such as a dog, a cat, or a mouse.

EXAMPLE

Hereinafter, the present invention will be described in more detail with reference to examples. However, it will be obvious to those skilled in the art that these examples are provided only for illustration of the present invention and should not be construed as limiting the scope of the present invention.

Example 1

Design of Dual Functional Peptide Having Both Cell Permeation and Bone Tissue Regeneration Ability Six peptide candidates which are expected to have dual functions of cellular permeability and bone regeneration ability were selected from among amino acid sequences of copine 7 proteins. The amino acid sequences for the six peptides are set forth in SEQ ID NOS: 1 to 6 in the following Table 1, and the positions thereof on the copine 7 protein are shown in FIG. 1. As shown in the following Table 1, the peptides set forth in SEQ ID NOS: 1, 2, 4 and 5 each consist of 10 amino acids, the peptide set forth in SEQ ID NO: 3 includes a peptide having the amino acid sequence set forth in SEQ ID NO: 2 and a peptide having the amino acid sequence set forth in SEQ ID NO: 4, which are connected to one another, and thus consists of 20 amino acids, and the peptide set forth in SEQ ID NO: 6 includes a peptide having the amino acid sequence set forth in SEQ ID NO: 4 and a peptide having the amino acid sequence set forth in SEQ ID NO: 5, which are connected to one another, and thus consists of 20 amino acids.

TABLE 1

Amino acid sequences of peptides set forth in SEQ ID NOS: 1 to 6

| | Position on copine 7 protein | Amino acid sequence (N terminus→C terminus) | Molecular weight |
|---|---|---|---|
| SEQ ID NO: 1 (CDP1) | 321-330 | STTFEEMQKA | 1170.5 |
| SEQ ID NO: 2 (CDP2) | 331-340 | FEEGQAQWDC | 1211.4 |
| SEQ ID NO: 3 (CDP3) | 331-350 | FEEGQAQWDCVNPKYKQKRR | 2509.2 |
| SEQ ID NO: 4 (CDP4) | 341-350 | VNPKYKQKRR | 1315.7 |
| SEQ ID NO: 5 (CDP5) | 351-360 | SYKNSGVVVL | 1064.5 |
| SEQ ID NO: 6 (CDP6) | 341-360 | VNPKYKQKRRSYKNSGVVVL | 2362.3 |

Example 2

Synthesis of Peptides

The peptides set forth in SEQ ID NOS: 1 to 6 were synthesized from the C-terminus by an Fmoc solid phase chemical synthesis method using a synthesizer. Rink resin (0.075 mmol/g, 100~200 mesh, 1% DVB crosslinking) conjugated with fmoc-(9-fluorenylmethoxycarbonyl) as a blocking group was used for the synthesis. 50 mg of Rink amide MBHA resin was added into the synthesizer, the resin was swollen with DMF and a 20% piperidine/DMF solution was used to remove the Fmoc-group. 5, 10 and 15 equivalents of a 0.5M amino acid solution (solvent: DMF), 1.0M DIPEA (solvent: DMF & NMP) and 0.5M HBTU (solvent: DMF) were reacted under a nitrogen atmosphere for one to two hours. Whenever the deprotection and coupling steps were completed, the reaction solution was washed twice with DMF and methanol. After the last amino acid was coupled, the Fmoc-group was removed by deprotection.

Figure 2:
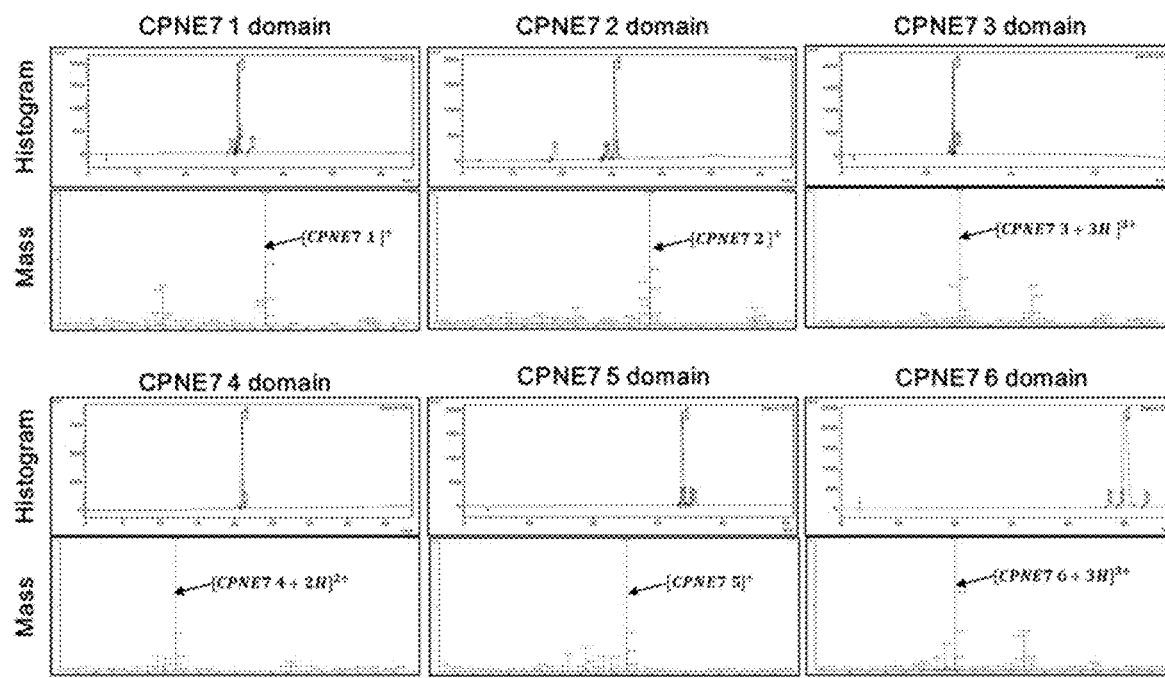
FIG. 2 shows results of HPLC and mass analysis to identify the results of solid-phase chemical synthesis of the peptides represented by the amino acid sequences set forth in SEQ ID NOS: 1 to 6.

Synthesis was identified through a ninhydrin test method. After identifying Fmoc group removal, a reagent K cleavage cocktail was added at a rate of 20 ml per 1 g of the resin, shaken for 3 hours and then filtered to separate the cocktail in which the resin and the peptide were dissolved. Cold ether was added to the filtered solution to precipitated peptide in cleavage cocktail and the peptide was separated by centrifugation. After washing several times with ether and centrifuging, the reagent K cleavage cocktail was completely removed. The crude peptide was obtained, dissolved in distilled water, and purified using liquid chromatography. The purified peptide was lyophilized. The molecular weight of the purified peptide was determined using mass spectrometry. FIG. 2 shows the results of HPLC and mass analysis on peptides of SEQ ID NOS: 1 to 6 synthesized by the method described above.

Example 3

Evaluation of In-Vitro Cytotoxicity of Synthetic Peptides

Figure 3:
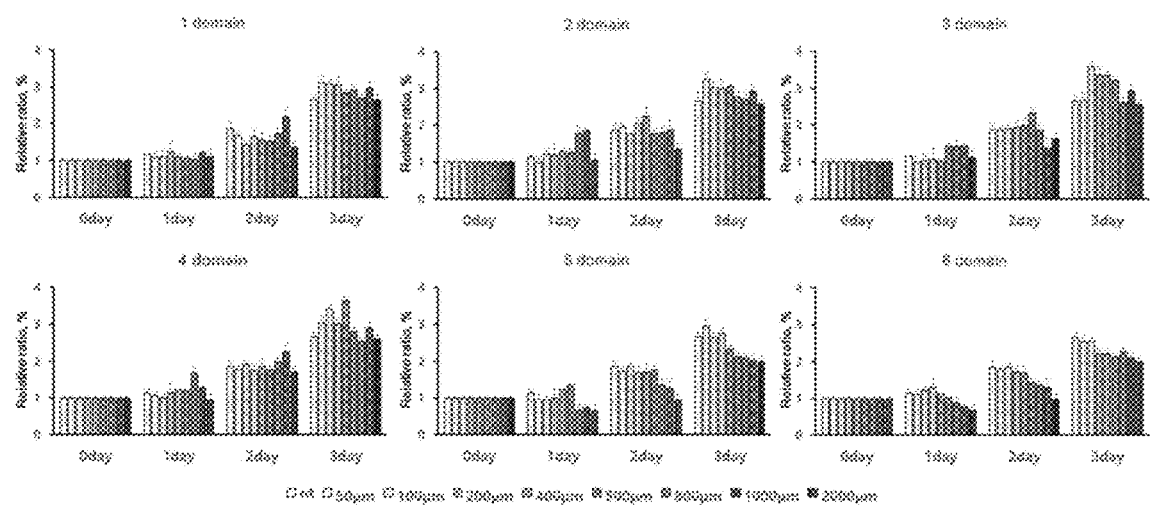
FIG. 3 shows the result of an MTT assay to evaluate the cytotoxicity of the peptides represented by the amino acid sequences set forth in SEQ ID NOS: 1 to 6.

A cell viability test was performed to evaluate the cytotoxicity of the peptides set forth in SEQ ID NOS: 1 to 6 synthesized in Example 2 above. For this purpose, dental pulp stem cells were seeded at a density of $9 \times 10^3$ cells per well into each well of a 96-well polystyrene plate in a Dulbecco's Modified Eagle's Medium (Gibco, USA) supplemented with 10% FBS (fetal bovine serum) and a 1% antibiotic-antimycotic solution (Thermo Fisher Scientific, USA), and then cultured for 24 hours. Each well was treated with various concentrations (50 µM, 100 µM, 200 µM, 400 µM, 500 µM, 800 µM, 1000 µM and 2000 µM) of the peptides set forth in SEQ ID NOS: 1 to 6. After 24 hours (1 day), 48 hours (2 days) and 72 hours (3 days), an MTT assay was performed to identify the cytotoxicity of the peptides. For the MTT assay, the medium was removed 24 hours, 48 hours, and 72 hours after treatment with peptide and each well was then treated with a mixture of 180 µl of a DMEM medium and 20 µl of a MTT solution, followed by further culturing for 1 hour. One hour later, the mixed solution was removed, each well was treated with 200 µl of dimethyl sulfoxide (DMSO) and the mixed solution was then transferred into a new 96-well plate and the cytotoxicity thereof was measured. All values were expressed as mean±standard deviation (SD) for triplicate experiments and the measured values are shown in FIG. 3.

As a result, it was identified that the peptide set forth in SEQ ID NO: 5 and the peptide set forth in SEQ ID NO: 6 were intracellularly toxic, and the peptides set forth in SEQ ID NOS: 1 to 4 did not have cytotoxicity, even if they were all cultured for 3 days.

Example 4

Identification of Cell Permeability of Synthetic Peptides

In order to identify the cell permeability of the peptides set forth in SEQ ID NOS: 1 to 6 synthesized in Example 2, fluorescein isothiocyanate (FITC) was attached to the N-terminus of each peptide. Dental pulp stem cells were seeded at a density of $3 \times 10^4$ cells into a 4-well chamber and cultured in DMEM medium for 24 hours for cell stabilization. 24 hours later, the cells were treated with the FITC-labeled peptide at various concentrations (50 µM, 100 µM, 200 µM, 500 µM, 1000 µM) for 30 minutes. The cells were treated with 100 ng/ml of copine 7 protein for 30 minutes in order to compare the cell permeability thereof with the peptide. Then, in order to compare the intracellular permeation behaviors of these peptides or the protein, each well was treated with 4% paraformaldehyde, fixed at room temperature for 10 minutes, treated with 0.5% Triton-X 100, and cultured at room temperature for 15 minutes. Then, the cells were blocked with a buffer solution (PBS) containing 3% bovine serum albumin (BSA) for 30 minutes. In the case of copine 7 protein, a CPNE7 primary antibody was diluted at a ratio of 1:100 in a buffer solution (PBS) containing 1% bovine serum albumin and reacted at 4° C. for 16 hours. A fluorescein isothiocyanate (FITC)-conjugated secondary antibody was diluted at a ratio of 1:200 and reacted at room temperature for 1 hour. Finally, the nuclei-staining dye (Hoechst 33342, blue) was treated at room temperature for 10 minutes and washed with a buffer solution (PBS), and the fluorescence intensity thereof was measured using a confocal scanning microscope (IX 70, Olympus Co, Tokyo, Japan) to determine the degree of expression. All values were expressed as mean±SD of the fluorescence intensities measured in three different areas, and were compared with the control group (no treatment, NT) (*P<0.05).

Figure 4:
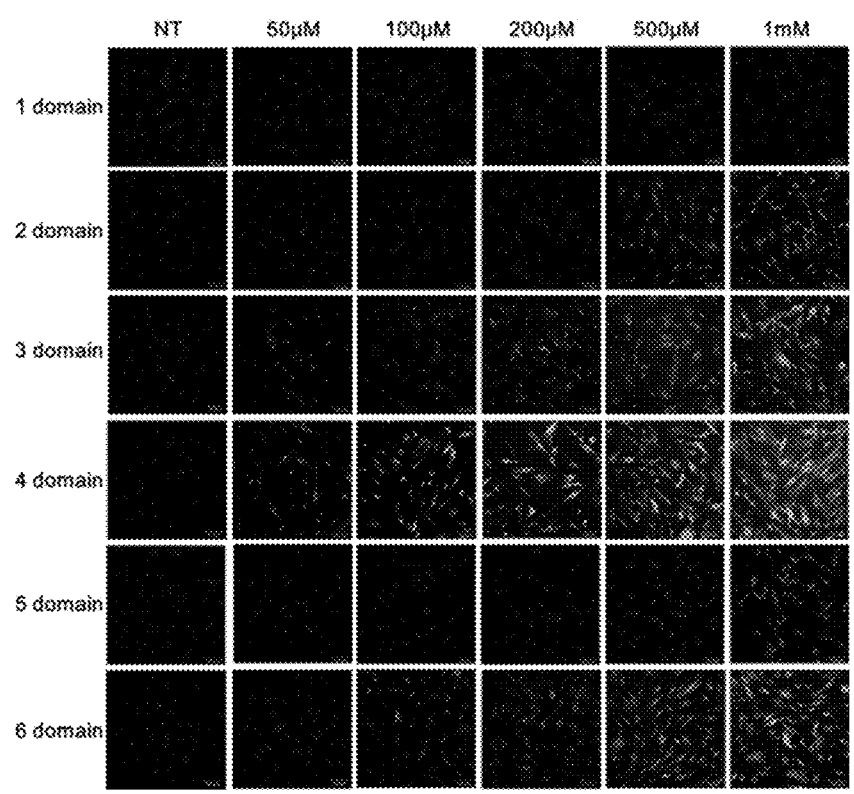
FIG. 4 shows the result of confocal microscopic observation to evaluate the cell permeability of the peptides represented by the amino acid sequences set forth in SEQ ID NOS: 1 to 6.

As a result, as shown in FIG. 4, it was found that the peptide set forth in SEQ ID NO: 1 had no fluorescence expression even at the highest concentration, 1000 uM, and thus had no cell permeation ability. On the other hand, it was found that the peptide set forth in SEQ ID NO: 2 had weak fluorescence even at 1000 uM, but did not have strong fluorescence. However, the peptide set forth in SEQ ID NO: 4 had fluorescence even when treated at 100 μM, which means that the peptide had the best cell permeation efficiency. Next, the peptide set forth in SEQ ID NO: 3 and the peptide set forth in SEQ ID NO: 6 were found to have relatively excellent cell permeation efficiency in this order.

Figure 5A:
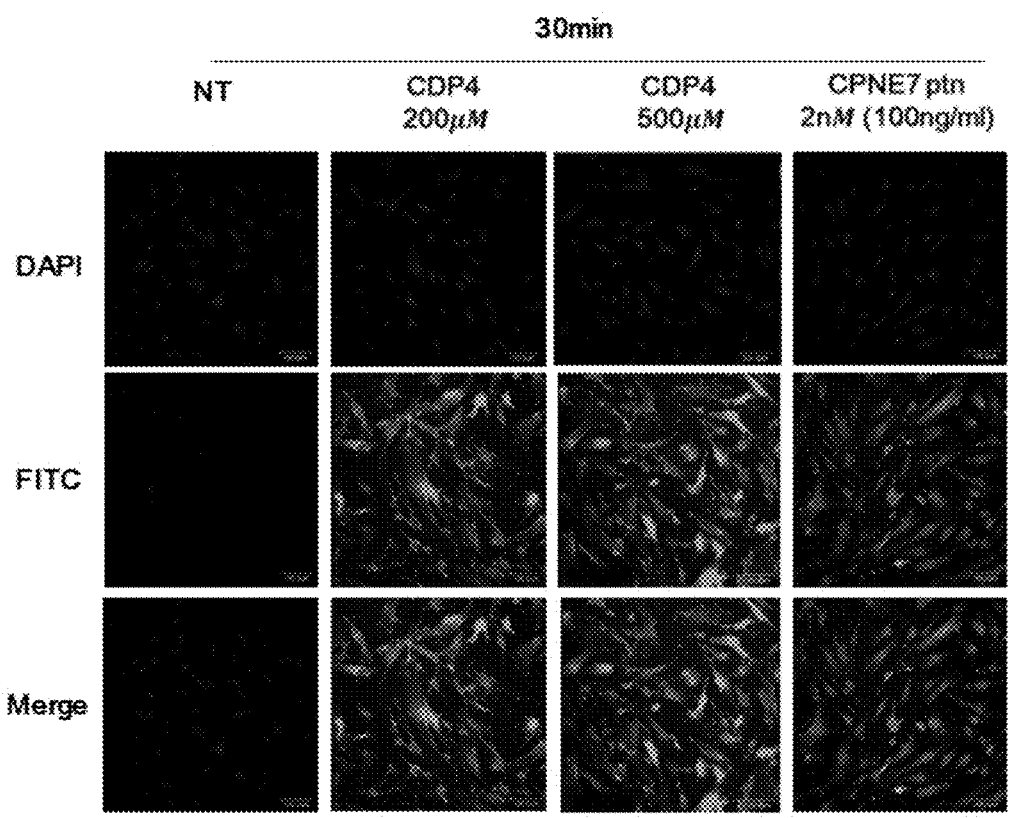
FIG. 5A shows the result of confocal microscopic observation and FIG. 5B shows the result of quantitative analysis to evaluate the cell permeability of the peptide represented by the amino acid sequence set forth in SEQ ID NO: 4 and copine 7 protein.
Figure 5B:
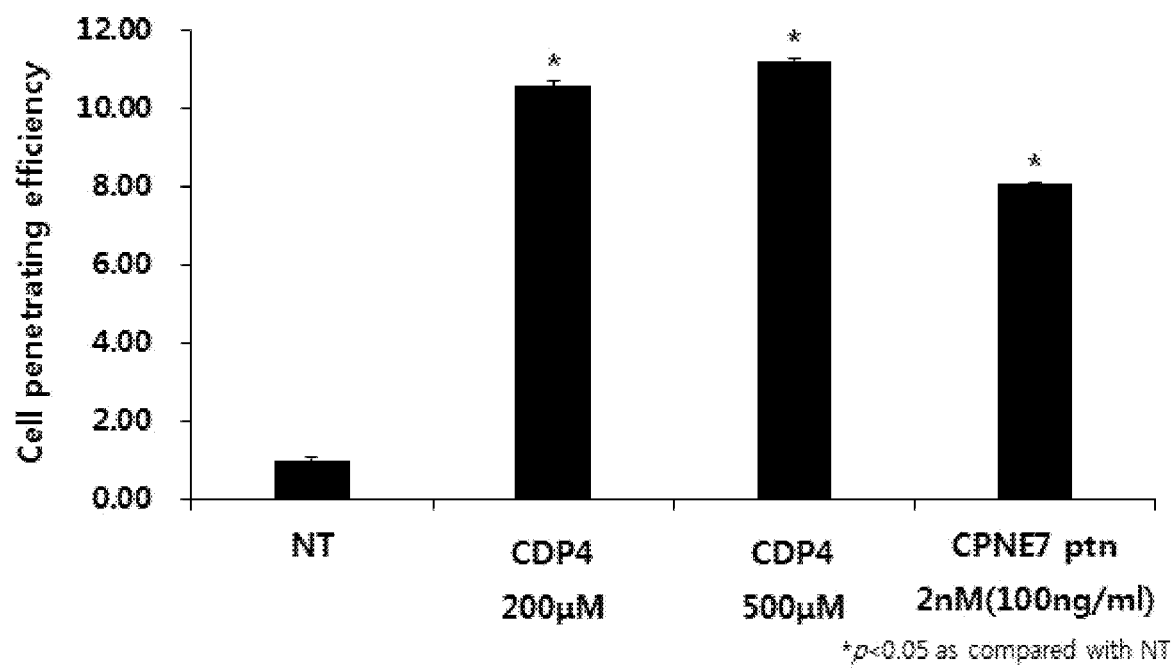

Meanwhile, when comparing the cell permeation ability of the peptide set forth in SEQ ID NO: 4 with that of copine 7 protein using a confocal microscope, it was found that the peptide set forth in SEQ ID NO: 4 had better cell permeability than the copine 7 protein. As a result of the quantification of the fluorescence intensity, the peptide set forth in SEQ ID NO: 4 exhibited strong fluorescence intensity compared to the copine 7 protein, which indicates that the peptide set forth in SEQ ID NO: 4 exhibited improved cell permeability compared to the copine 7 protein, from which the peptide derived (FIG. 5).

Example 5

Comparison of Bone Differentiation Ability Between Peptide Set Forth in SEQ ID NO: 4 and Copine 7 Protein In order to identify the bone differentiation ability of the peptide set forth in SEQ ID NO: 4, which was determined to have the best cell penetration function in Example 4, and the copine 7 protein, expression difference of osteocalcin in dental pulp stem cells (DPSCs) was evaluated.

For this purpose, $1 \times 10^5$ DPSCs were suspended in 50 μl of a medium (Dulbecco's Modified Eagle's Medium, Gibco, USA) supplemented with 10% FBS (fetal bovine serum) and a 1% antibiotic-antimycotic solution (Thermo Fisher Scientific, USA) in a 24-well plate. The cells were cultured for 24 hours and then treated with the peptide set forth in SEQ ID NO: 4 at concentrations of 200 μM and 500 μM and the copine 7 protein at a concentration of 100 ng/ml, respectively, while replacing the medium with Differentiation basal medium-Osteogenic (Lonza, USA) supplemented with a supplement (hMSC Osteogenic SingleQuots, Lonza, USA) for 18 days. Then, the expression level of osteocalcin was compared using an immunofluorescence (IF) technique. For this purpose, the cells were treated with 4% paraformaldehyde, fixed at room temperature for 10 minutes, treated with 0.5% Triton-X 100, and cultured at room temperature for 15 minutes. Then, the cells were blocked with a buffer solution (PBS) containing 3% bovine serum albumin (BSA) for 30 minutes. The primary antibody of osteocalcin was diluted at a ratio of 1:100 in a buffer solution (PBS) containing 1% bovine serum albumin and reacted at 4° C. for 16 hours. An fluorescein isothiocyanate (FITC)-conjugated secondary antibody was diluted at a ratio of 1:200 and reacted at room temperature for 1 hour. Finally, the cells were treated with the nuclei-staining dye (Hoechst 33342, blue) at room temperature for 10 minutes and washed with buffer (PBS), and the expression level of osteocalcin was determined with a confocal scanning microscope (IX 70, Olympus Co, Tokyo, Japan). All values were expressed as mean±SD of fluorescence intensity measured in three different areas and were compared with the control group (no treatment, NT) (*P<0.05).

Figure 6A:
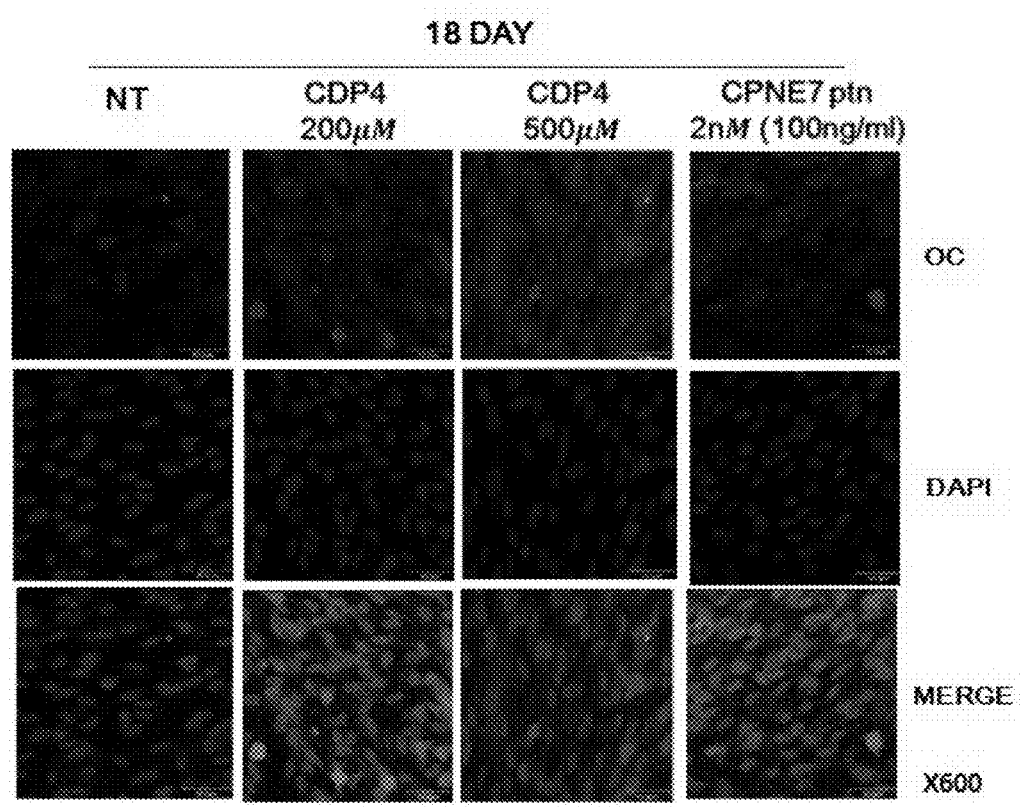
FIG. 6A shows the results of confocal microscopic observation and FIG. 6B shows the result of quantification of the expression level of osteocalcin to compare the bone differentiation ability between the peptide represented by the amino acid sequence set forth in SEQ ID NO: 4 and copine 7 protein.
Figure 6B:
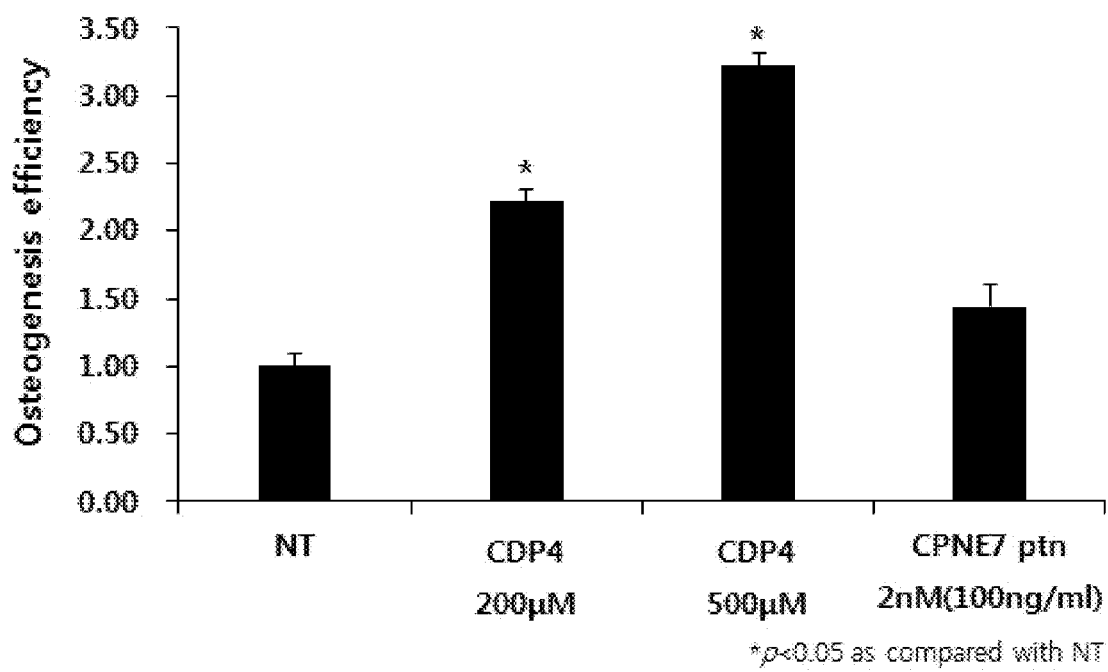

As a result, as shown in FIG. 6, when the expression degree of osteocalcin was determined as a fluorescence intensity with a confocal microscope, groups treated with 200 μM and 500 μM of the peptide set forth in SEQ ID NO: 4 had relatively stronger fluorescence intensity than the group treated with 100 ng/ml of the peptide. As a result, it was found that the peptide set forth in SEQ ID NO: 4 was superior to the copine 7 protein in terms of bone differentiation ability.

Example 6

Evaluation of Bond Regeneration Ability of Peptide Set Forth in SEQ ID NO: 4 and Copine 7 Protein in Rabbit 20 mg and 40 mg of the peptide shown in SEQ ID NO: 4 were dissolved in 100 μL of purified water, and the solution was added to 0.1 g of a bone graft material, allowed to stand at 4° C. for 24 hours and lyophilized. The copine 7 protein was used as a control group in the same manner as above and was incorporated in amounts of 100 μg and 200 μg in 0.1 g of a bone graft material. A defect part with a diameter of 8 mm was formed in the skull of a New Zealand white rabbit (cuniculus) and implanted with 0.1 g of a bone graft material in each defect part. The periosteum and skin were double-sutured. The animal was sacrificed 3 weeks after graft, and the specimen was fixed in a formalin solution and embedded in tissues to obtain a specimen with a thickness of 20 um. The prepared specimen was stained with basic fuchsin and toluidine blue to prepare a non-decalcified sample. The sample was imaged with an optical microscope and analyzed histologically. All values were expressed as mean±SD (SD) of areas measured in three different samples and compared with copine 7 protein (*P<0.05).

Figure 7A:
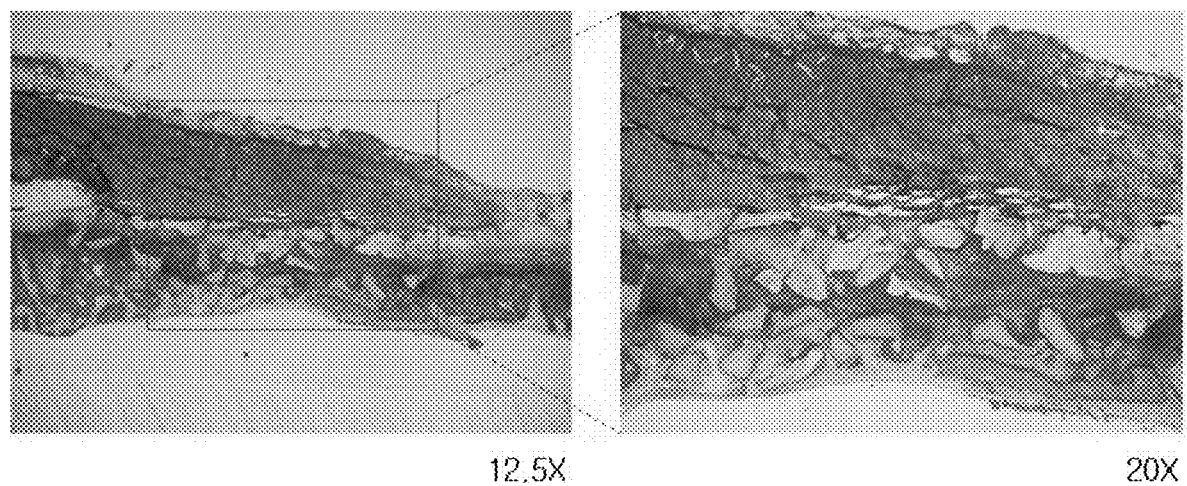
FIG. 7A shows the result of identification of a bone tissue regeneration effect after grafting a bone graft material containing the peptide represented by the amino acid sequence set forth in SEQ ID NO: 4 or copine 7 protein into the skull of a rabbit
Figure 7A:
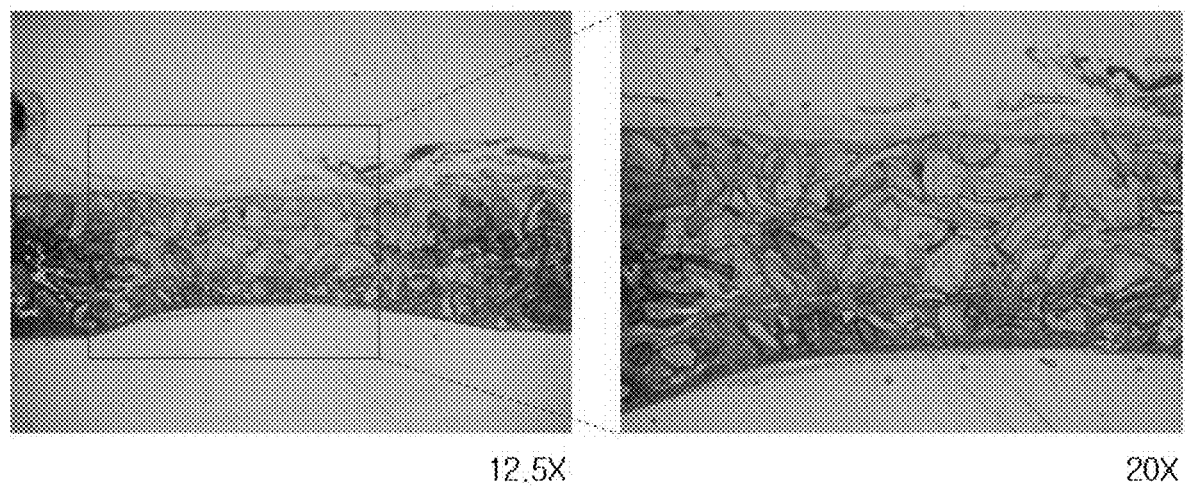
Figure 7A:
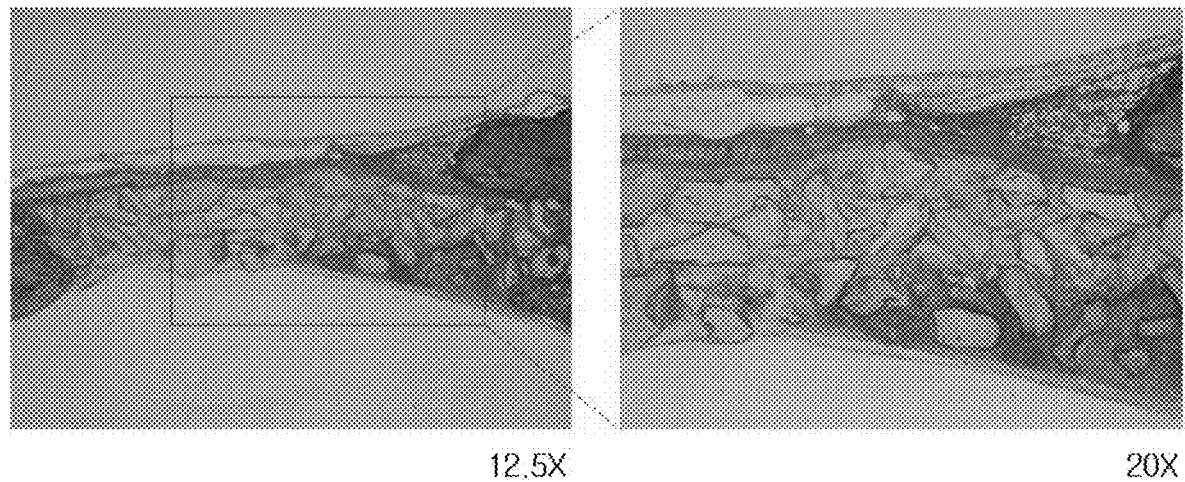
Figure 7A:
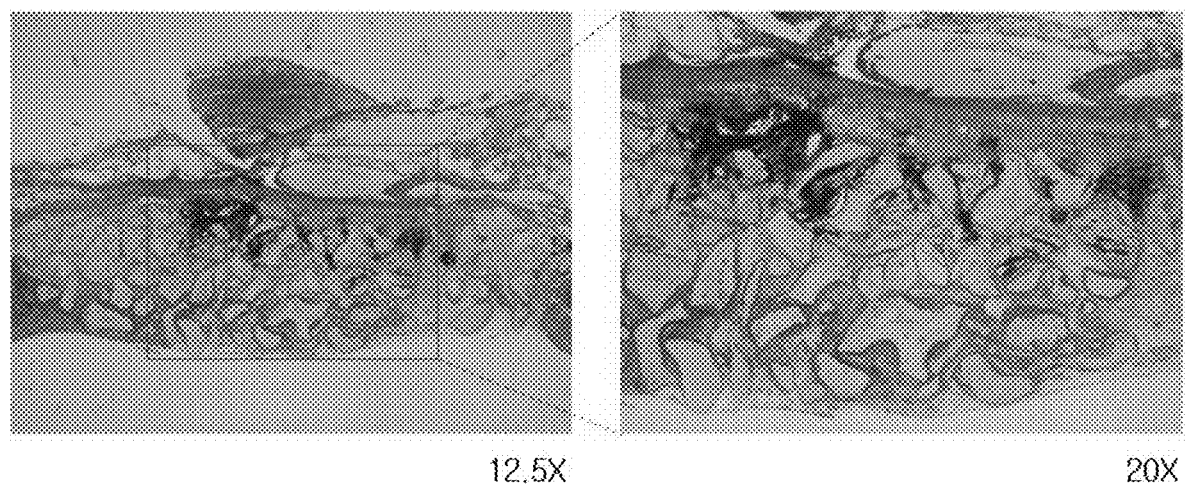
Figure 7B:
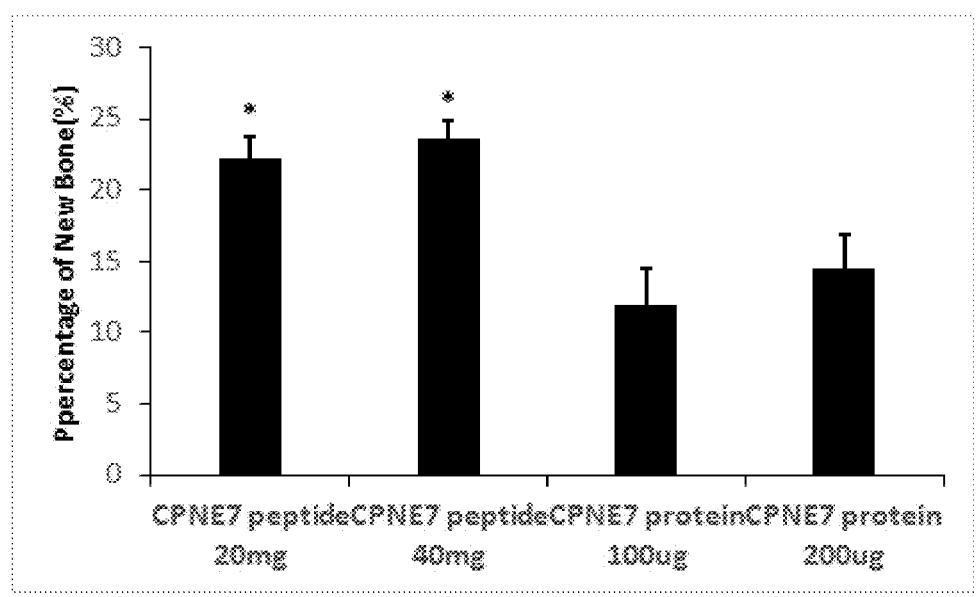
FIG. 7B shows the result of histomorphometric measurement of a bone tissue regeneration area after grafting a bone graft material containing the peptide represented by the amino acid sequence set forth in SEQ ID NO: 4 or copine 7 protein into the skull of the rabbit.

As a result, as shown in FIG. 7A, a bone graft material containing the peptide set forth in SEQ ID NO: 4 had an excellent effect of regenerating new bone, based on the skull defect part, compared to a bone graft material containing copine 7 protein. Also, as shown in FIG. 7B, when histomorphometric analysis was performed, it was found that the peptide set forth in SEQ ID NO: 4 had a significantly wider bone regeneration area than the copine 7 protein. These results indicate that the peptide set forth in SEQ ID NO: 4 has an excellent bone regeneration effect compared to copine 7 protein.

Although the present invention has been described in detail with reference to specific configurations, those skilled in the art will appreciate that this description is provided as preferred embodiments for illustrative purposes and should not be construed as limiting the scope of the present invention. Therefore, the substantial scope of the present invention is defined by the accompanying claims and equivalents thereto.

INDUSTRIAL APPLICABILITY

The peptide according to the present invention is useful for the treatment of diseases requiring bone generation, such as osteoporosis, due to excellent bone regeneration ability, and does not need to attach an additional peptide or add other agent for cell permeation of the peptide due to the intrinsic cell permeation ability thereof, promotes cell migration, proliferation and differentiation in a short time due to the intrinsic cell permeation ability thereof, and ultimately demonstrates an effective bone regeneration effect. Thus, advantageously, the peptide according to the present invention can be easily applied to various surgical regenerative treatments including orthopedic surgery and can shorten the treatment period.

SEQUENCE LISTING FREE TEXT

An electronic file is attached.

The invention claimed is:

1. A peptide consisting of the amino acid sequence of SEQ ID NO: 4(VNPKYKQKRR), wherein one or more amino acid is D-type amino acid.

2. The peptide according to claim 1, wherein the peptide has dual functions of cell permeability and bone tissue regeneration ability.

3. A method for regenerating bone tissue, the method comprising administering a pharmaceutical composition comprising a peptide consisting of the amino acid sequence of SEQ ID NO: 4 or grafting a biomaterial comprising a peptide consisting of the amino acid sequence of SEQ ID NO: 4 to a subject in need of bone tissue regeneration.

4. The method according to claim 3, wherein the composition is formulated as the one selected from the group consisting of a formulation for oral administration, a formulation for injection, and a gel formulation for topical implantation.

5. The method according to claim 4, wherein the gel formulation for topical implantation comprises:
  i) a synthetic polymer selected from the group consisting of polylactic glycolic acid, a poloxamer and propylene glycol; or
  ii) a natural polymer selected from the group consisting of collagen, alginic acid, propylene glycol alginate, chondroitin sulfate and chitosan.

6. The method according to claim 3, wherein the composition is administered at a dose of 1 to 60 mg per 1 kg of a body weight of a subject in need of treatment.

7. A biomaterial comprising a peptide consisting of the amino acid sequence of SEQ ID NO: 4, and a chemically synthesized bone mineral or synthetic polymer.

8. The biomaterial according to claim 7, wherein the chemically synthesized bone mineral is hydroxyapatite.

9. The biomaterial according to claim 7, wherein the synthetic polymer is selected from the group consisting of polylactic glycolic acid, a poloxamer and propylene glycol.

* * * * *

UNITED STATES PATENT AND TRADEMARK OFFICE
CERTIFICATE OF CORRECTION

PATENT NO. : 10,836,795 B2
APPLICATION NO. : 16/464099
DATED : November 17, 2020
INVENTOR(S) : Yoon Jeong Park et al.

It is certified that error appears in the above-identified patent and that said Letters Patent is hereby corrected as shown below:

In the Specification

The following paragraph should be inserted at Column 2, Line 47, after the heading BRIEF DESCRIPTION OF THE DRAWINGS:
--The patent or application file contains at least one drawing executed in color. Copies of this patent or patent application publication with color drawing(s) will be provided by the Office upon request and payment of the necessary fee.--

Signed and Sealed this
Fifth Day of January, 2021

Andrei Iancu
*Director of the United States Patent and Trademark Office*